(12) United States Patent
Nyi

(10) Patent No.: US 7,637,883 B2
(45) Date of Patent: Dec. 29, 2009

(54) WRIST BRACE AND METHOD FOR ALLEVIATING AND PREVENTING WRIST PAIN

(76) Inventor: Franklin H. Nyi, 23409 Broadwell Ave., Torrance, CA (US) 90502

(*) Notice: Subject to any disclaimer, the term of this patent is extended or adjusted under 35 U.S.C. 154(b) by 0 days.

(21) Appl. No.: 11/746,242

(22) Filed: May 9, 2007

(65) Prior Publication Data

US 2008/0281242 A1   Nov. 13, 2008

(51) Int. Cl.
  *A61F 5/00*   (2006.01)
  *A61F 13/00*  (2006.01)
(52) U.S. Cl. .............................. 602/21; 602/20; 602/64
(58) Field of Classification Search ................... 602/20, 602/21, 60, 64, 22; D34/190, 192; 128/877–881; 2/20; 606/201, 204
See application file for complete search history.

(56) References Cited

U.S. PATENT DOCUMENTS

| D274,557 S | 7/1984 | Griffith, III |
| 5,063,913 A | 11/1991 | Nyi |
| 5,078,728 A | 1/1992 | Giarratano |
| 5,267,943 A * | 12/1993 | Dancyger ...................... 602/5 |
| 5,404,591 A * | 4/1995 | Brinnand et al. ................. 2/20 |
| 5,415,624 A * | 5/1995 | Williams ..................... 602/21 |
| 5,468,220 A * | 11/1995 | Sucher ........................ 602/21 |
| 5,695,520 A | 12/1997 | Bruckner et al. |
| 5,709,647 A | 1/1998 | Ferber |
| 5,769,808 A * | 6/1998 | Matthijs et al. ............... 602/64 |
| 5,774,424 A | 6/1998 | Yoo |
| 5,810,753 A * | 9/1998 | Eberbach ..................... 602/21 |
| 5,865,775 A | 2/1999 | Peoples et al. |
| 5,921,949 A * | 7/1999 | Dray .......................... 602/64 |
| 6,120,472 A * | 9/2000 | Singer, Jr. .................... 602/64 |
| 6,361,550 B2 | 3/2002 | Grey et al. |
| 6,517,501 B1 | 2/2003 | Slautterback |
| 6,755,800 B2 | 6/2004 | Weaver et al. |
| 7,037,285 B2 | 5/2006 | Yewer, Jr. |
| 7,037,286 B1 | 5/2006 | Reinhardt |
| 7,172,566 B2 | 2/2007 | Weaver, II et al. |
| 2003/0139698 A1* | 7/2003 | Hyson ........................ 602/61 |

* cited by examiner

*Primary Examiner*—Kim M Lewis
(74) *Attorney, Agent, or Firm*—Fulwider Patton LLP

(57) ABSTRACT

A wrist brace includes a flexible main body having one or more pressure transmitting members disposed thereon designed to impart focused pressure on a tendon of interest.

12 Claims, 6 Drawing Sheets

WRIST BRACE AND METHOD FOR ALLEVIATING AND PREVENTING WRIST PAIN

BACKGROUND OF THE INVENTION

The present invention relates generally to wrist braces, and more particularly, to a flexible wrist brace for alleviating the symptoms associated with wrist injuries, such as carpal tunnel syndrome and ulnar neuritis, without restricting the wearer's ability to grasp objects and perform daily tasks. Additionally, the present invention is directed to methods for alleviating and preventing wrist pain associated with such wrist injuries.

Many people suffer from injury to the soft tissues of the wrist and carpal tunnel, often caused by frequent, sustained repetitive motion involving the hands. Repetitive activities which require the same or similar hand/wrist action can result in injuries which have been collectively referred to as Cumulative Repetitive Stress Syndrome or Repetitive Strain Injury. The most familiar and common of such wrist injuries is known as carpal tunnel syndrome which produces pain, discomfort, nerve conduction disturbances, and impairment of function of the hand and sometimes the arm as well. The most common symptoms of this condition include intermittent pain and numbness of the hand.

Carpal tunnel syndrome occurs when the median nerve, which runs from the forearm into the hand, becomes pressed or squeezed at the wrist. The median nerve provides feeling in one's thumb, along with the index, middle and ring fingers. The median nerve controls sensations to the palmar side of the thumb and these fingers as well as impulses to some muscles in the hand which allow the fingers and thumb to move. The median nerve receives blood, oxygen and nutrients through a microvascular system which is present in the connective tissue surrounding the nerve fiber. Increased pressure on the nerve fiber can constrict these microvessels and will reduce the blood flow to the median nerve. Any prolong deprivation of oxygen and nutrients can result in severe nerve damage.

The median nerve passes through the carpal tunnel, a canal in the wrist surrounded by the carpal bones on three sides and a fibrous sheath called the transverse carpal ligament ("flexor rethinaculum") on the fourth side. In addition to the median nerve, the nine flexor tendons in the hand pass through this canal. When compressed, the median nerve will cause pain, weakness or numbness in the hand and wrist which may also radiate up along the arm. The median nerve can be compressed by a decrease in the size of the carpal canal itself or an increase in the size of its contents (i.e., such as the swelling of the flexor tendons and the lubrication tissue surrounding these flexor tendons), or both. For example, conditions that irritate or inflame the tendons can cause them to swell. The thickening of irritated tendons or swelling of other tissue within the canal narrows the carpal canal, causing the median nerve to be compressed. The cross-sectional area of the tunnel also changes when the hand and wrist changes positions. Wrist flexion or extension can decrease the cross-sectional area, thus increasing the pressure exerted on the median nerve. Flexion also causes the flexor tendons to somewhat rearrange which can also compress the median nerve. For example, simple bending of the wrist at a 90° angle will decrease size of the carpal canal. Without treatment, carpal tunnel syndrome can lead to chronic neural muscular disorders of the hand and sometimes the arm.

While carpal tunnel syndrome is generally associated with repetitive motion involving the hands, physiology and family history may also play significant roles in a person's susceptibility to the injury. For example, the disorder is sometimes due to a congenital predisposition, namely, that the carpal tunnel is simply smaller in some people than in others. Other contributing factors include trauma or injury to the wrist that cause swelling, such as a sprain or fracture. Over activity of the pituitary gland, physiological problems in the wrist joint itself, work stress, fluid retention during pregnancy or menopause and diseases such as diabetes, rheumatoid arthritis or thyroid disease are still additional sources which may lead to the carpal tunnel syndrome.

Treatment for carpal tunnel syndrome may include non-surgical and surgical procedures. Treatments for carpal tunnel syndrome should begin as early as possible to prevent the occurrence of more severe symptoms. Non-surgical treatments include the restriction of the motion of the wrist by immobilizing braces or splints; controlling the pain and swelling by administering anti-inflammatory drugs, such as aspirin, ibuprofen and other non-prescriptive pain relievers; administering diuretics to decrease swelling; and injecting the wrist with pain killer such as corticosteroids or the drug lidocaine. Other non-surgical treatments include, but are not limited to, applying heat or cold to the effective site to promote repair of the injured tissue; performing physical therapy to the hand and wrist to reduce the stress on the wrist; adopting a more ergonomic work and life environment; and avoiding or curtailing the hand motion which produces the inflammation in the first place. If the symptoms cannot be treated with non-surgical intervention, then surgery may be required. Carpal tunnel release is one of the most common surgical procedures performed in the United States to treat carpal tunnel syndrome. This surgery involves severing the transverse carpal ligament to relieve the pressure on the median nerve. Surgery is usually done under local anesthetic and usual does not require an overnight hospital stay.

Another painful injury to the wrist is ulnar neuritis which, like carpal tunnel syndrome, results in numbness, tingly, a burning sensation and pain in the hands and fingers. The ulnar nerve, like the median nerve, can be impinged and irritated at the wrist. The ulnar nerve runs down the ulnar (small finger) side of the wrist. It supplies sensation to the small and ring fingers as well as controls some small muscles of the hand. Similar factors as those seen with carpal tunnel syndrome can contribute to ulnar neuritis. Direct pressure on the nerve for long periods of time, such as biking, is a significant contributor to the problem. Trauma or a fall on the palm may also bring about symptoms. The ulnar tunnel (also referred to as Guyon's canal) is a canal in the wrist that contains both the ulnar nerve and the ulnar artery. Compression of the ulnar nerve, like compression of the median nerve, can cause similar symptoms as carpal tunnel syndrome. This syndrome is much less common then carpal tunnel syndrome yet both conditions can occur at the same time. The numbness caused by these two syndromes effect the hand in different locations. When the median nerve is compressed in carpal tunnel syndrome, pain and numbness spread into the thumb, index finger, middle finger and half the ring finger. Compression of the ulnar nerve in the Guyon's canal usually causes numbness in the pinky and half of the ring finger. Non-surgical treatment for ulnar neuritis is similar to carpal tunnel syndrome. If all attempts to control the symptoms utilizing non-surgical techniques fail, then surgery may be needed to reduce the pressure on the ulnar nerve.

One way to prevent the onset of carpal tunnel syndrome is to prevent the swelling or inflammation of the flexor tendons (the flexor digitorum superficialis tendons and flexor digitorum profundus tendons) which extend through the carpal tunnel. Additionally, prevention of inflammation to the flexor tendon sheath and the lubrication tissue surrounding the flexor tendons will help to alleviate compression of the median nerve. Additionally, there are other tendons surrounding the carpal tunnel which also can become inflamed and swollen and could exert additional pressure on the median nerve. These tendons include the palmaris longus tendon, the flexor carpi radialis tendon and the flexor carpi ulnaris tendon. The palmaris longus tendon can become swollen and can cause additional pressure on the median nerve due to its close proximity thereto. The same is true of the flexor carpi radialis tendon. In the case of ulnar neuritis, should the flexor carpi ulnaris tendon become swollen and inflamed, its proximity to the ulnar nerve can be a source of increased pressure on the ulnar nerve. Therefore, the prevention of the inflammation and swelling of these wrist tendons serves as a good treatment for preventing carpal tunnel syndrome and ulnar neuritis.

The swelling and inflammation of the flexor tendons and tendons within in the wrist of a person is often caused by the stretching and outward movement of the tendons within the wrist as the wrist flexes and extends and fingers move. In this regard, the tendon has a tendency to stretch and move in an outwardly fashion away from the carpal bones in the wrist which can cause the tendon sheath, and the tendon itself, to become swollen or inflamed when this same motion is repeated again and again. This constant stretching of the tendon in both a longitudinal and an outward direction is a primary cause of the inflammation and swelling of the tendon and tissue in the wrist area. Prolonged and continuous subjection of the tendons to this repetitive motion only causes additional stretching of the tendons and surrounding tissue and only increases the pain. Irritation and swelling of the tendon can be alleviated by preventing the tendon from stretching and moving outwardly in the first place.

As mentioned above, one approach to lessening the pain associated with carpal tunnel syndrome and ulnas neuritis is to restrain the wrist to prevent the repetitive hand motions which cause the discomfort in the first place. In this regard, many wrist braces have been develop to address the need to confine the wrist and forearm in an immobilized position. While such braces or splints do somewhat reduce continued injury to the median nerve and ulnar nerve by restraining this wrist, such wrist braces and splints usually restrict the motion of the fingers and flexion and extension of the wrist. Such braces and splints can prevent the wearer from properly grasping objects and performing normal daily tasks utilizing the affected hand.

What have been needed and heretofore unavailable are improved wrist brace and methods for alleviating and reducing the adverse results caused by injuries to the wrist, such as carpal tunnel syndrome and ulnar neuritis. Such a device and method should eliminate the disadvantages and shortcomings associated with prior developed braces and splints. Preferably, the brace device should be lightweight and relatively simple in construction to allow the user to wear the brace device without much interference to the wearer's ability to flex the wrist and manipulate the fingers in a normal fashion. It should be designed so that the device can be easily placed on the hand with a minimal need to reposition the brace on the wrist in response to hand and wrist motion. Also, it would be beneficial and economical if the wrist brace could be worn on either hand of the individual. The present inventions disclosed herein satisfy these and other needs.

SUMMARY OF THE INVENTION

In general terms, the present invention is directed to a novel wrist brace construction that utilizes pressure transmitting members designed to impart localized and direct pressure on specific tendons that are more vulnerable to stretching and developing injury to the wrist. In this manner, the present invention is designed to help prevent the unwanted stretching of the wrist tendons along with the associated inflammation and discomfort associated with a wrist injury. The wrist brace includes a flexible main body which is adapted to be wrapped around the hand/wrist of the wearer. Pressure transmitting members are disposed along the main body of the wrist brace at particular locations where the pressure transmitting members will be strategically placed over the tendons of interest once the wrist brace is placed around the wrist of the wearer. In one aspect of the invention, the flexible main body can be snuggly wrapped around the user's hand/wrist to allow the pressure transmitting members to impart localized and focused pressure on specific tendons of interest. The size and shape of these pressure transmitting members are selected such that the pressure transmitting member applies most of the focused pressure on the tendon itself while only a small amount of focused pressure will be actually be applied in the area surrounding the tendon. In one aspect of the present invention, the flexible main body includes means for varying the amount of focused pressure which can be developed by the pressure transmitting members. For example, a hook and loop fastener (i.e. Velcro fastener) can be used to allow the wearer to change the amount of inward pressure developed by the wrist brace and the pressure transmitting members. Such an element allows the wearer to increase or decrease the amount of focused pressure developed by simply positioning the loop fastener to vary the snugness that the flexible main body impart to the wearer's hand/wrist.

In one aspect of the invention, the pressure transmitting member is designed to provide localized and focused pressure directly onto the flexor tendons which extend through the carpal tunnel. These flexor tendons includes the flexor digitorum superficialis tendons and flexor digitorum profundus tendons. The pressure transmitting member is disposed on the flexible main body of the wrist brace and is adapted to apply the focused pressure to the flexor tendons in the region of the transverse carpal ligament, which forms part of the carpal tunnel. In this regard, the pressure transmitting member provides sufficient amount of radial force or focused pressure on these particular tendons to prevent them from stretching outwardly during physical activity. As a result, normal trauma and stretching that usually occurs during physical activity are diminished since the pressure transmitting member helps to maintain these tendons from stretching outwardly, thus helping to prevent the tendons from becoming swollen or inflamed. This same pressure transmitting member also will apply focused pressure to the palmaris longus tendon since this tendon lies directly over the flexor tendons above the transverse carpal ligament and should help to prevent inflammation or swelling of this tendon as well.

In another aspect of the invention, additional pressure transmitting members are disposed on the flexible main body forming the wrist brace to apply focused pressure on other tendons in the wrist, such as the flexor carpi radialis tendon, which extends outside of the carpal tunnel but is none the less susceptible to the same outward stretching that can cause swelling and inflammation of this tendon as well. Another pressure transmitting member can be disposed on the flexible main body forming the wrist brace to apply focused pressure on the flexor carpi ulnaris tendon in order to help prevent ulnar neuritis from developing in the wrist. Although the flexor carpi ulnaris tendon is not located directly in Guyon's canal, the swelling or inflammation of this tendon can lead to compression of the ulnar nerve which is the cause of ulnar neuritis. Prevention of the swelling of this particular tendon can reduce pressure to be placed on the ulnar nerve.

The present invention also utilizes a pressure transmitting member disposed on the main body to apply focused pressure to the tendons on the backside of the wrist, which are also susceptible to stretching that can cause inflammation and pain. This pressure transmitting member is designed to extend over and apply focused pressure to the extensor digitorum tendons and the extensor indicis tendon along the region of the extensor retinaculum ligament. This pressure transmitting member should help to prevent the unwanted stretching of these tendons during physical activity.

The wrist brace of the present invention is designed to allow the wearer to maintain almost full use of his/her fingers, along with near normal flexion and extension of the wrist, while the wrist brace is being worn. As a result, the wearer can assume normal activities with his/her hand while preventing tendons from becoming swollen or inflamed even if when performing repetitive hand/wrist motions which would otherwise result in such swelling and inflammation. A wrist brace in accordance with the present invention is thus useful in alleviating the wrist pain associated with wrist injuries, including, but not limited to carpal tunnel syndrome and ulnar neuritis since the wrist brace helps to present the stretching of the tendons which is the primary cause of the wrist injury in the first place. As a result, the use of the wrist brace, in conjunction with another non-surgical treatment, such as taking anti-inflammatory drugs, will greatly diminish the pain and discomfort associated with wrist injuries. Additionally, the wrist brace of the present invention can be used before the onset of any wrist injury or pain. An individual can wear the wrist brace when performing repetitive hand motions or engaging in other activities which would otherwise lead to wrist injury since there is little loss of normal motion of the wrist and fingers when wearing the present invention.

A method for alleviating or preventing wrist pain includes providing a wrist brace having pressure transmitting members which apply focused pressure to the flexor tendons in the region of the transverse carpal ligament. Other methods include applying focused pressure to the flexor carpi ulnaris tendon and the other tendons, either separately or together in various combinations.

These and other advantages of the present invention become more apparent from the following detailed description of the invention, when taken in conjunction with the accompanying exemplary drawings.

DETAILED DESCRIPTION OF THE PREFERRED EMBODIMENTS

Figure 1:
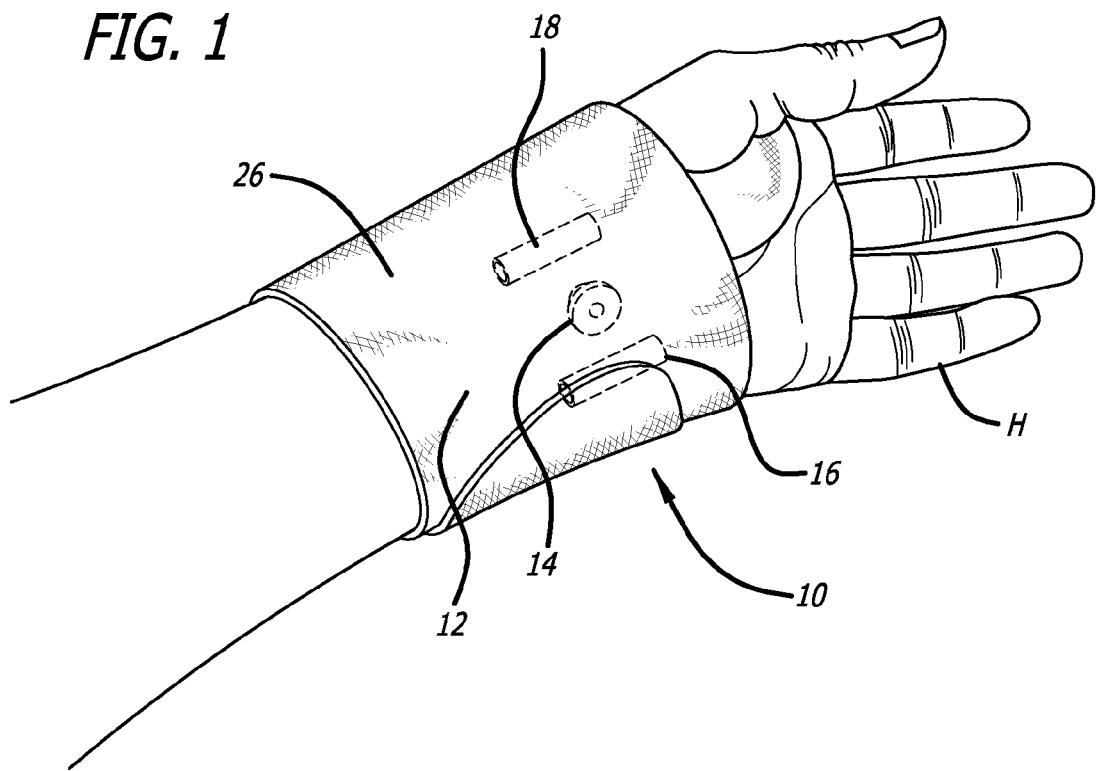
FIG. 1 is a perspective view of an embodiment of a wrist brace made in accordance with the present invention as it is mounted on a wearer's wrist and hand, showing the palmar side of the wearer's hand, with the pressure transmitting members of the wrist brace in phantom, as indicated by broken in lines, as these members contact the wrist of the wearer to apply focused pressure to the underlying tendons.
Figure 2:
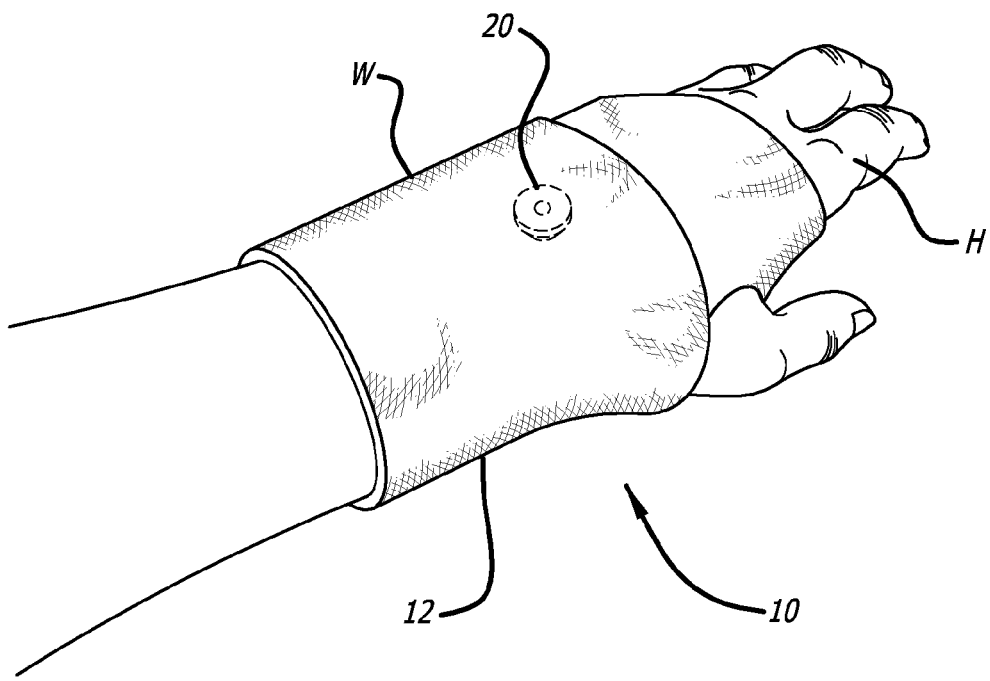
FIG. 2 is a perspective view of the wrist brace of FIG. 1 depicting the backside of the hand and wrist of the wearer, showing an additional pressure transmitting member in phantom, as indicated by broken in lines, as the member contacts the back side of the wrist of the wearer to apply focused pressure to the underlying tendons.

Referring now to FIGS. 1-6, an embodiment of a wrist brace made in accordance with the present invention is generally designated by the reference numeral 10. The wrist brace 10 includes a flexible main body 12 that is designed to wrap around the hand (H)/wrist(W) of the wearer. The wrist brace 10 includes pressure transmitting members 14-20 which are disposed on the flexible main body 12 and are adapted to apply localized and focused pressure to certain tendons in the wrist. The identification of these tendons and the anatomy of the wrist will be addressed in greater detail below. The particular construction of the particular wrist brace 10 shown in FIGS. 1-6 allows the wrist brace 10 to be worn on either the left or right wrist of the wearer.

Figure 3:
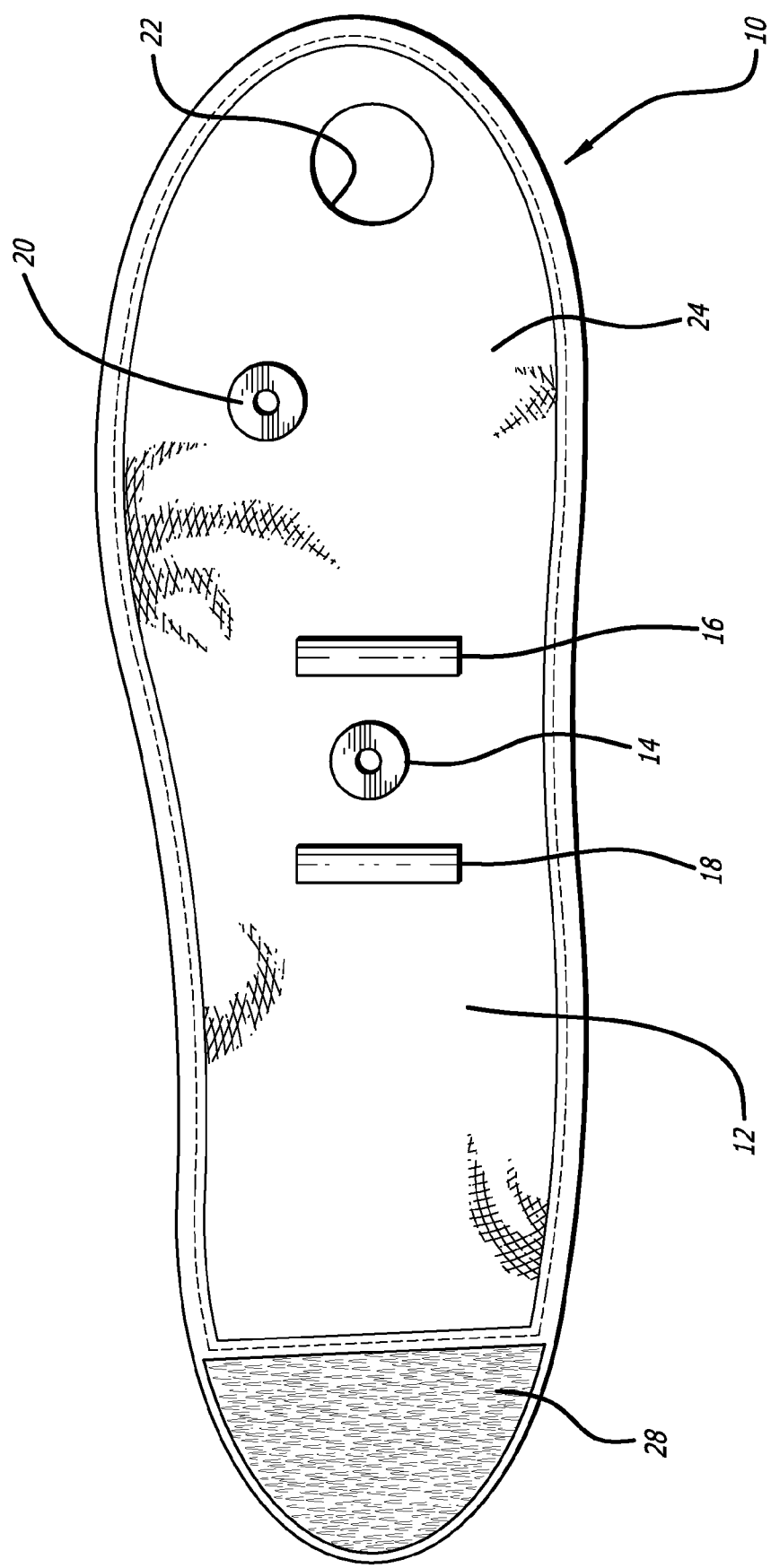
FIG. 3 is a top view of the wrist brace of FIG. 1 showing the force transmitting members attached to inner surface of the flexible, main body of the wrist brace.

Referring specifically now to FIG. 3, the flexible main body 12 is shown as an elongate structure having a thumb opening 22 formed therein. This flexible main body 12 includes an inner surface 24, shown in FIG. 3, and an outer surface 26, shown in FIGS. 1 and 2. The inner surface 24 is designed to come in direct contact with the user's hand and has the pressure transmitting members 14-20 connected thereto. The thumb opening 22 is located at one end of the flexible main body 12 and the other end has a hook fastener 28 attached thereto. In use, this hook fastener 28 is designed to come in contact with the outer surface 26 of the main body, as is shown in FIG. 1, in order to maintain the wrist brace in place. The outer surface 26 can be made from a suitable "loop" material which cooperates with the hook fastener 28 to hold the main body 12 snugly in place on the wearer. This hook and loop fastener also allows the wearer to adjust the amount of snugness that is imparted by the wrist brace to the wearer. The flexible main body 12, in turn, helps to achieve an inward force or pressure which acts on each of the pressure transmitting member 14-20 to allows these members 14-20 to apply the focused pressure onto the tendons of interest. Accordingly, the wearer can adjust the amount of focused pressure being imparted by the pressure transmitting members 14-20 by simply adjusting the snugness imparted by the flexible main body. The hook and loop fastener system provides just one simple and convenient mechanism for adjusting the snugness imparted by the flexible main body 12. It will be appreciated by those skilled in the art that other fastening means and components besides the hook and loop fastener system shown on the embodiment of FIGS. 1-6 could be utilized to maintain the wrist brace 10 snuggly wrapped around the wearer's hand/wrist.

Figure 4:
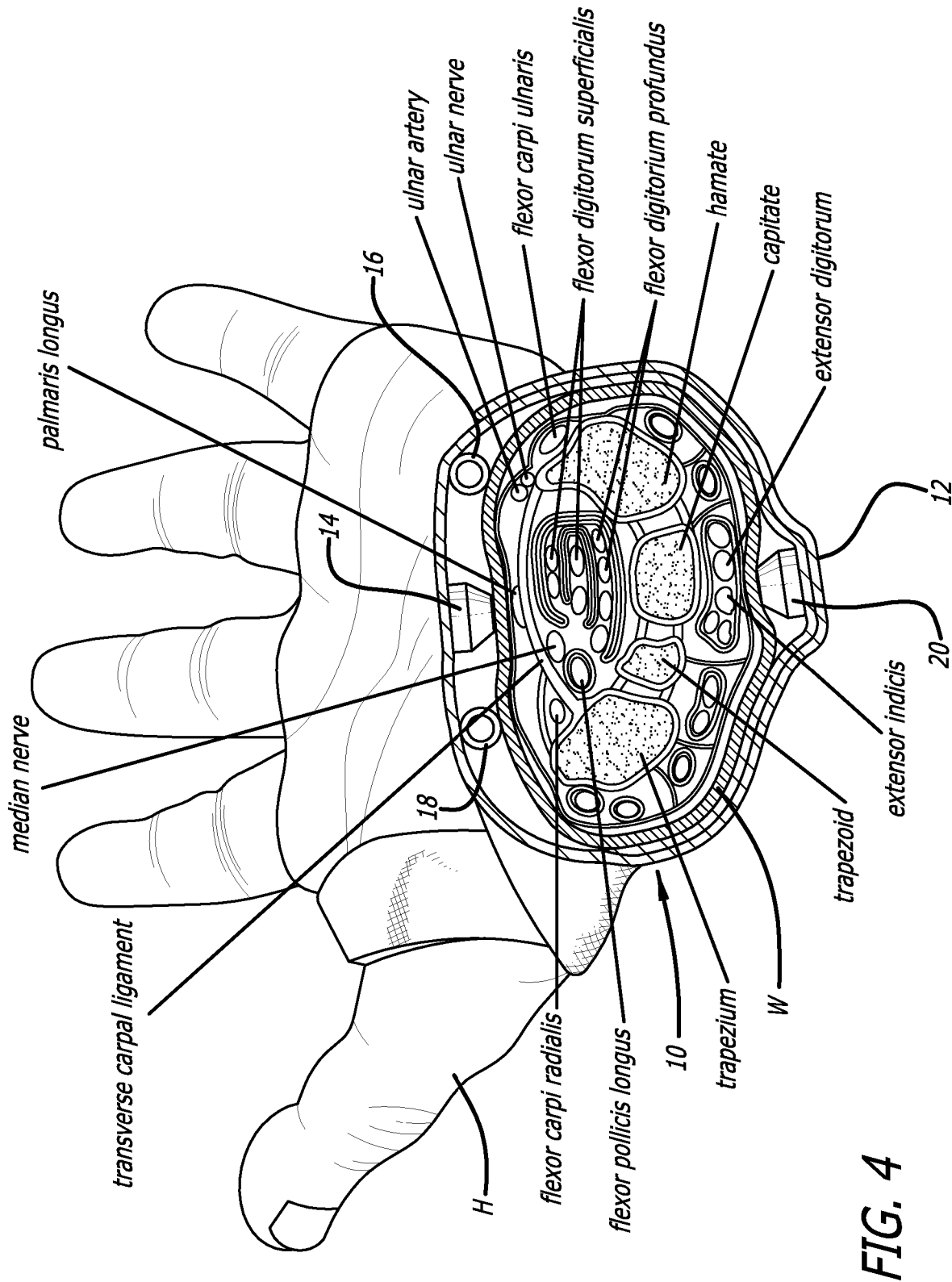
FIG. 4 is a transverse, cross-sectional view of the wearer's wrist showing the carpal tunnel, Guyon's canal and the wrist brace of FIG. 1 demonstrating the various force transmitting members applying focused pressure to the various tendons in the wrist.

Referring now specifically to FIG. 4, a cross sectional view of the wearer's wrist is shown which generally depicts the anatomy of wrist and the various tendons found in the wrist, along with the placement of the pressure transmitting members 14-20 associated with the wrist brace 10. The carpal tunnel is generally shown as it is formed by the carpal bones, namely, the hamate, capitate, trapezoid and trapezium bones on three sides and the transverse carpal ligament (flexor retinaculum) on the palmar side of the hand. The median nerve and the flexor tendons extend through the carpal tunnel as is shown in FIG. 4. The flexor tendons include the flexor digitorum superficialis tendons and flexor digitorum profundus tendons, which are generally bundled together, along with the flexor pollicis longus tendon which is located next to the median nerve. The palmaris longus tendon is located outside of the carpal tunnel and directly above the transverse carpal ligament. The flexor carpi radialis tendon is located outside of the carpal tunnel, but in close proximity to the median nerve. The ulnar nerve and artery are found in Guyon's canal located outside of, an to the top right, of the carpal tunnel. The flexor carpi ulnaris tendon is shown positioned below the ulnar nerve and artery directly above the hamate bone. On the backside of the hand, the extensor digitorum tendons and the extensor indicis tendon are shown collectively behind the capitate bone.

In FIG. 4, the wrist brace 10 is shown with the pressure transmitting elements 14-20 directly over the tendons of interests. As can be seen in FIG. 4, the middle force transmitting member 14 is placed directly over the flexor digitorum superficialis tendons and flexor digitorum profundus tendons located in the carpal tunnel. This pressure transmitting element 14 also contacts the palmaris longus tendon due to its proximity above the carpal tunnel. In this regard, this pressure transmitting member 14 maintains a focused pressure on these various tendons to prevent them from stretching outwardly during repetitive wrist and finger motions. This particular pressure transmitting member 14 is shown having a disc-like shape which allows the member 14 to extend over all of these tendons of interest in order to provide the focused pressure needed to prevent the tendons from stretching outward when certain hand motions are made. Accordingly, the size and shape of this forced transmitting member 14 are designed basically to cover the area needed to apply the focused pressure directly onto these tendons. As can best be seen in FIG. 5, this pressure transmitting member 14 is placed over the region of the transverse carpal ligament. The length and width of the pressure transmitting element 14 can be varied such that this pressure is designed to act primarily on the tendons of interest. Although this forced transmitting member 14 is shown generally as a disc-like structure, it will be apparent to those skilled in the art that many other shapes and sizes of the pressure transmitting member could be utilized in accordance with the present invention.

Figure 5:
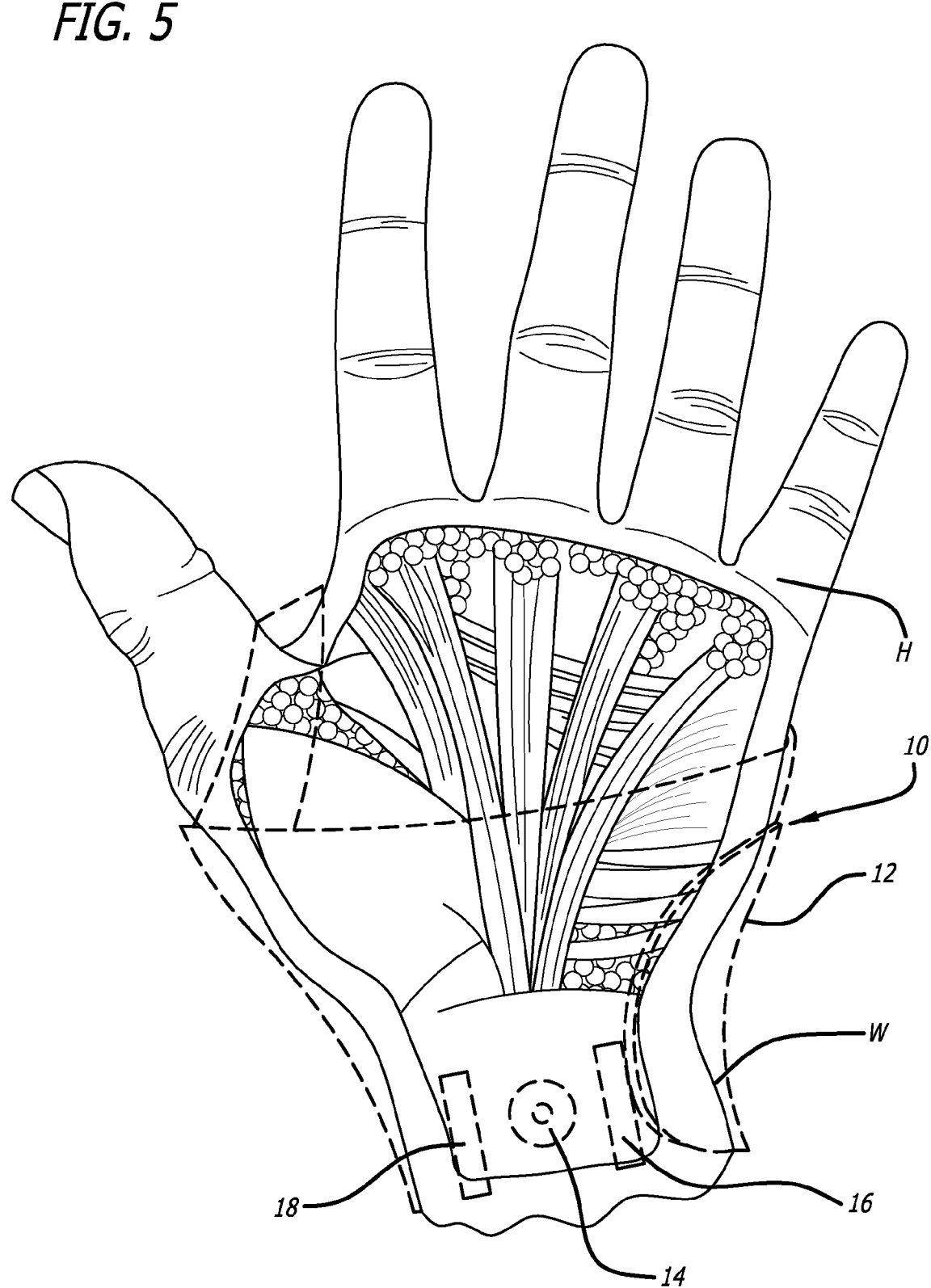
FIG. 5 is a partially cut away view of the palmar portion of the wearer's hand showing the placement of the wrist brace of FIG. 1 with the force transmitting members in phantom, as indicated by broken lines.

The second pressure transmitting member 16, shown in FIGS. 1, 4 and 5, is utilized to place forced pressure on the flexor carpi ulnaris tendon in order to prevent ulnar neuritis from developing. This particular pressure transmitting member 16 is designed to extend over the portion of the flexor carpi ulnaris tendon which extends outside of the transverse carpal ligament. Unlike the first-mentioned pressure transmitting member 14 which requires a larger contact area, this particular pressure transmitting member 16 has a tubular shape which generally reduces the contact area that is needed to place focused pressure onto the flexor carpi ulnaris tendon. Again, it should be appreciated that other sizes and shapes could be utilized in accordance with the present invention to create the pressure transmitting member 16. Additionally, if the pressure transmitting member has a smaller contact area, then the wrist brace should provide more wrist flexibility to the wearer since there would be less structural elements in the way. A smaller contact area also helps to reduce the amount of focused pressure that would be applied to tissue and structure surrounding the tendon.

The third pressure transmitting member 18 disposed on the flexible main body 12 on the palmar side of the hand is positioned to provide focused pressure to the flexor carpi radialis tendon in the wrist. Again, while the flexor carpi radialis tendon does not extend within the carpal tunnel, its close proximity to the median nerve could cause compression to the medial nerve should this particular tendon become swollen or inflamed from repetitive hand/wrist motion. This particular pressure transmitting member 18, like the second pressure transmitting member 16 discussed above, is shown as a cylindrically shaped structure in order to create a particular contact area which focuses the pressure almost directly onto the tendon of interest. Like the other pressure transmitting elements 14 and 16, the size and shape of this particular pressure transmitting member 18 can be modified, as needed, in order to create the desired contact area needed to maintain the tendon from stretching outwardly.

Figure 6:
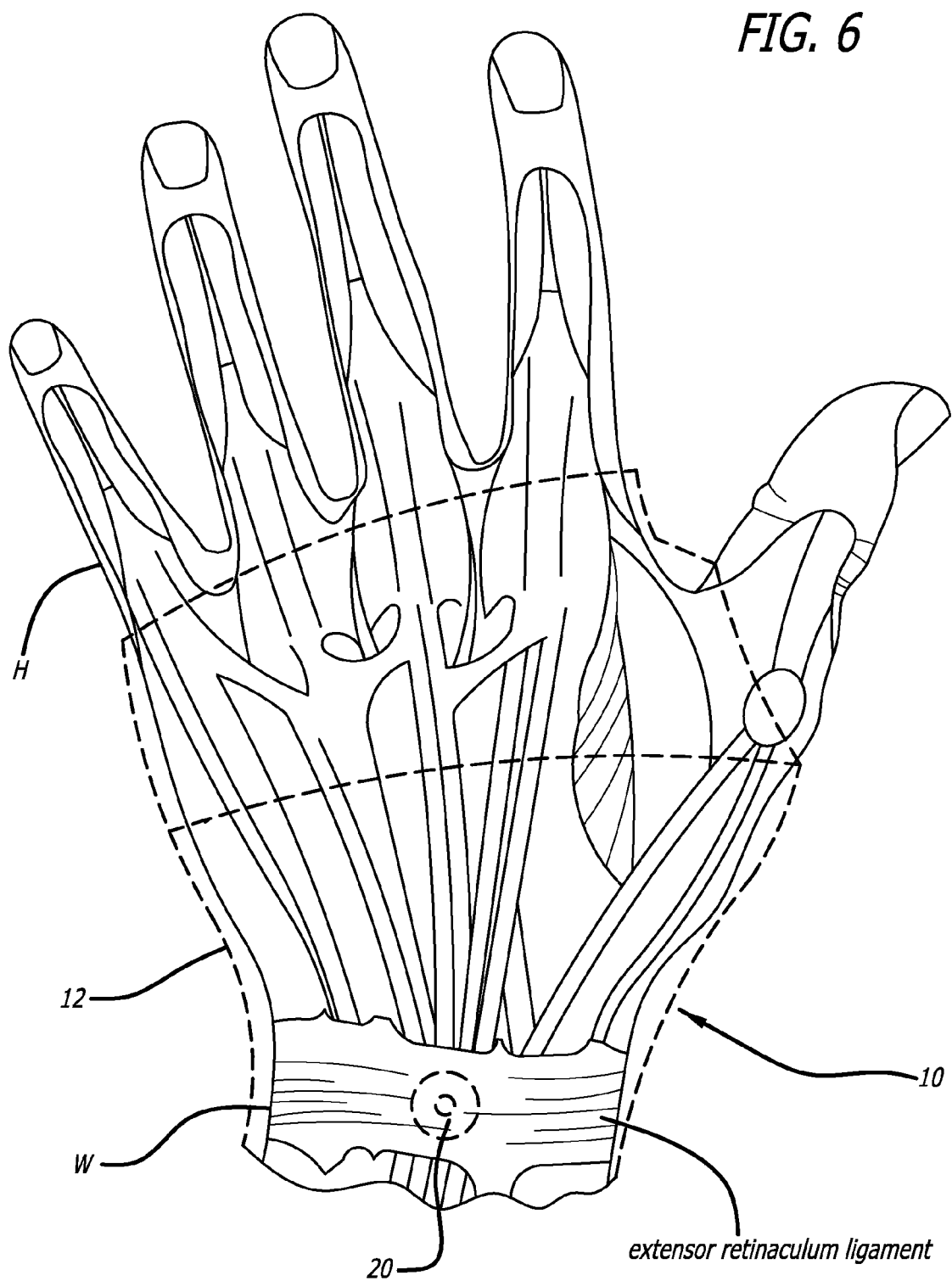
FIG. 6 is a partially cut away view of the backside of the wearer's hand showing the wrist brace of FIG. 1 with the force transmitting member in phantom, as indicated by broken lines.

Another pressure transmitting element 20, shown disposed on the flexible main body 12 on the backside of the hand in FIGS. 4 and 6, places focused pressure on the extensor digitorum tendons and the extensor indicis tendon. FIG. 6 shows the general placement of the pressure transmitting member 20 over the extensor retinaculum ligament which extends over the extensor digitorum tendons and the extensor indicis tendon. This particular pressure transmitting member 20 is shown having a circular, disc-like shape in order to create a suitable contact area which primarily focuses pressure to these tendons only. Again, the size and shape can be varied to obtain the desired contact area needed to properly focus the pressure against these tendons of interest.

Figure 7:
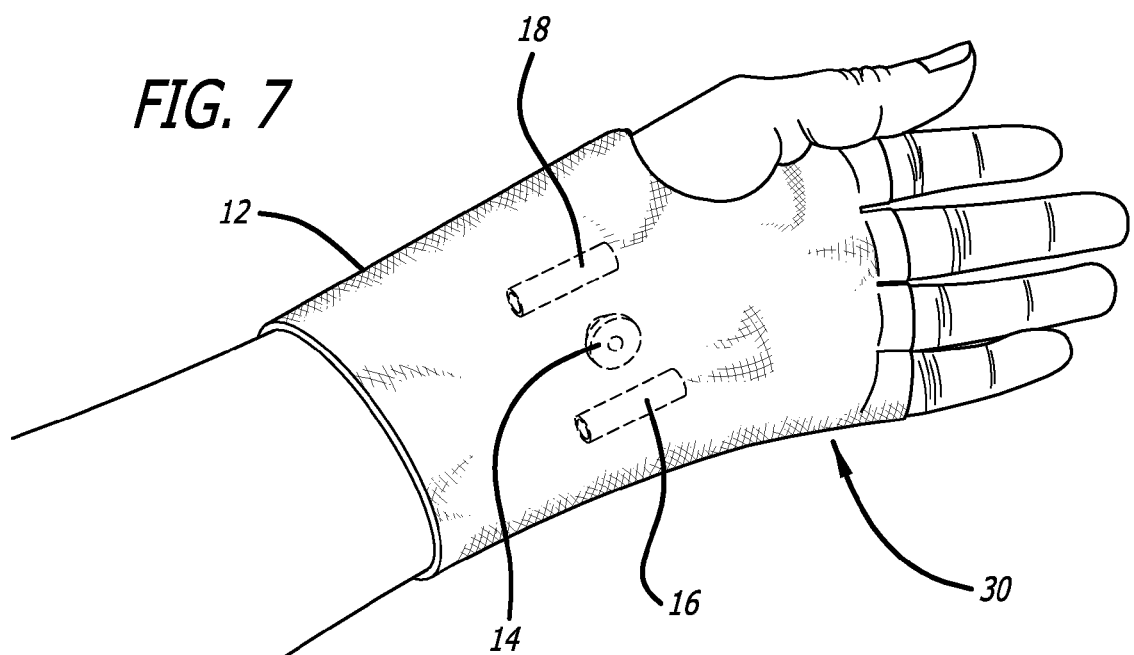
FIG. 7 is a perspective view of another embodiment of a wrist brace made in accordance with the present invention as it is mounted on a wearer's wrist and hand, showing the palmar side of the wearer's hand with the pressure transmitting members of the wrist brace in phantom, as indicated by broken in lines, as these members contact the wrist of the wearer to apply focused pressure to the underlying tendons.

FIG. 7 shows another embodiment of the present invention in which the wrist brace 30 takes the form of a glove-like structure and includes the pressure transmitting members associated with the particular wrist brace shown in FIGS. 1-6. In this particular embodiment of the invention, the flexible main body 12, formed as a glove (with or without finger sleeves), maintains the pressure transmitting members 14-20 in proper position over the respective tendons. The glove may include straps (not shown) which allows the wearer to adjust the force imparted by the pressure transmitting members. This embodiment shows just one of the numerous forms that the wrist brace can be made in accordance with the present invention. Others include, but are not limited to, the formation of the flexible main body as a sleeve like structure which allows the wearer to slip the sleeve over the wearer's hand in order to place the pressure transmitting elements 14-20 in proper position over the tendons of interest. Such a sleeve-like structure may include straps, or other fastening devices, to increase or decrease the amount of pressure applied by the sleeve and pressure transmitting members on the wrist of the wearer.

Figure 8:
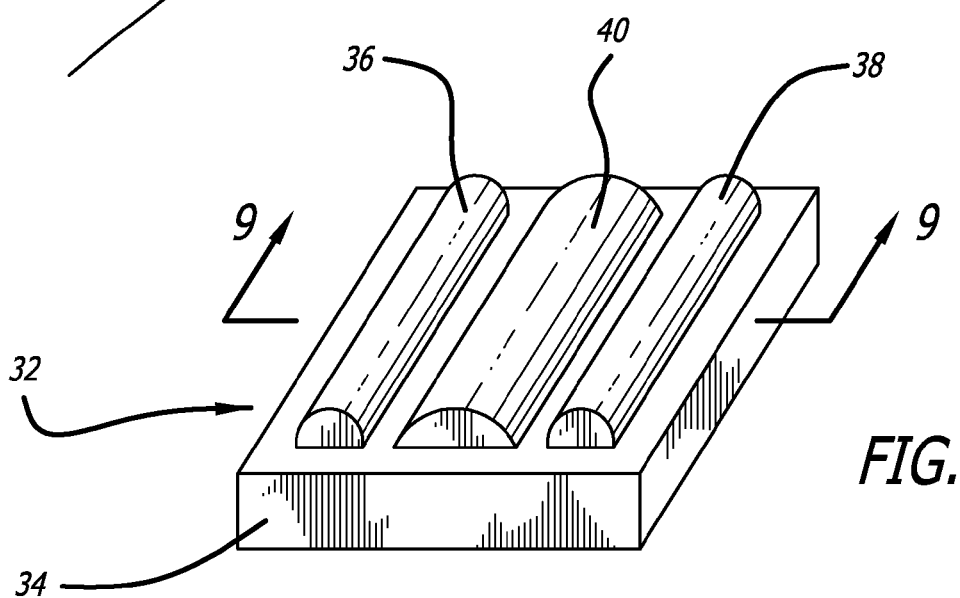
FIG. 8 is a perspective view of another embodiment of a force transmitting member made in accordance with the present invention.
Figure 9:
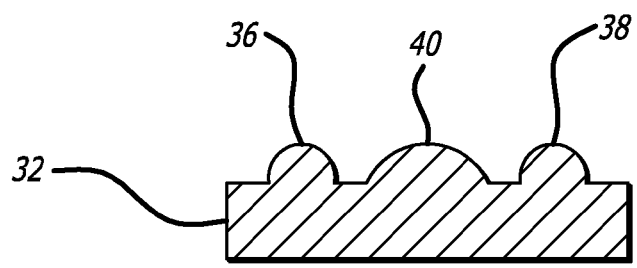
FIG. 9 is a cross sectional view of the focused force transmitting member of FIG. 8 taken along lines 9-9.

Referring now to FIGS. 8 and 9, a particular embodiment of a pressure transmitting member 32 is disclosed. In this particular embodiment, individual pressure transmitting members are integrally connected via a single base 34 which can, in turn, be attached to the inner surface of the flexible main body. This structure eliminates the need to attach separate pressure transmitting members, such as the ones shown in FIGS. 1-6, to reduce the manufacturing steps needed to produce a commercial wrist brace made in accordance with the present invention. As can be seen in FIG. 8, the base 34 includes three raised projections 36-40 which act as the pressure transmitting members in accordance with the present invention. As can be seen in FIGS. 8 and 9, the size and shape of these raised projections 36-40 can be varied, as needed to create the contact area needed to apply the focused pressure to the respective tendons of interest. This embodiment shown in FIGS. 8 and 9 shows just one of the many ways in which the forced transmitting members can be manufactured in accordance with the present invention and used in conjunction with the flexible main body. This embodiment of force transmitting member 32 could be used with any of the embodiments of the main body disclosed and described herein.

Preferably, the main body 12 can be made from an elastic material which is capable of stretching and applying an inward force or pressure on the pressure transmitting members in order to allow the pressure transmitting members to impart the focused pressure on the tendons of interest. Suitable materials include, but are not limited to, neoprene, which may be terrycloth covered, spandex, and other elastic materials well known in the industry. The main body can be formed in the shape shown in FIGS. 1-6 or similar shapes. The flexible main body can be made from a commercially available hand/wrist wrap, such as one sold by Becton, Dickinson & Co. under the trademark ACE® and disclosed in FIGS. 1-6. Still other similar type wrist wraps could be utilized as the main flexible main body which forms part of the wrist brace of the present invention. The flexible main body can be made from a non-elastic material, if desired, however, components for applying force on the pressure transmitting members (straps, fasteners and the like) may be required.

The pressure transmitting members disclosed herein can be made from a rigid or simi-rigid material which, in cooperation with the flexible main body, imparts focused pressure onto the tendons of interests. In this regard, the pressure transmitting elements could be made out of suitable plastic materials, wood, metal and any other suitable material which will provide sufficient stiffness to allow the wrist brace to apply focused pressure to the tendons. Again, as previously mentioned, the size, shape and location of the various pressure transmitting members can be varied, as needed, in order to apply the focused pressure to the particular tendons of interest, in part, due to the different hand/wrist sizes of the wearers. Additionally, while only four individual pressure transmitting members are shown in the embodiments, additional or less pressure transmitting members could be used. It should be appreciated that the wrist brace, and the method of alleviating wrist pain in accordance with the present invention, can use a single pressure transmitting member disposed on a main body or can be made with different combinations of the pressure transmitting members disclosed herein. For example, if an individual is only suffering from ulnar neuritis, a single pressure transmitting member could be disposed on the flexible main body to impart focus pressure only onto the flexor carpi ulnaris. The wrist brace could be made with any number of different combinations of pressure transmitting members which will deliver the focus pressure to the desired tendons of interests.

The pressure transmitting members can be secured to the flexible main body by using any one of a number of fastening techniques. For example, the members could be adhesively bonded to the inner surface of the main body using adhesives and well known bonding materials. The main body could include pockets or pouches which house the pressure transmitting members. Alternatively, the members could be attached using hook and loop fasteners which allow the members to be removed and replaced on the main body to ensure that the members are properly aligned over the tendon(s) of interest. For example, the inner surface of then main body could include loop material which fastens onto hook fasteners attached to the underside of the pressure transmitting members. In this fashion, the pressure transmitting members can be removed and reattached to the inner surface as desired.

While the invention has been illustrated and described herein, in terms of a wrist brace and method for alleviating and preventing wrist pain, it will be apparent to those skilled in the art that the methods of the present invention could be incorporated with other devices. Additionally, the wrist brace with pressure transmitting members can be formed in other structural configurations as well. Further, other modifications and improvements can be made without departing from the scope of the present invention. While particular forms of the invention have been described and illustrated, it will be apparent to those skilled in the art that various modifications may be made without departing from the spirit and scope of the invention.

I claim:

1. A wrist brace, comprising:
a flexible main body having an outer surface and an inner surface, the main body being adapted to be worn on a hand and wrist of the wearer with the inner surface in contact with the hand during use; and when in use, a plurality of unconnected, distinct pressure transmitting members apply focused pressure to the tendons of the wrist,
wherein a first pressure transmitting member is disposed on the main body and adapted to apply focused pressure to the flexor digitorum superficialis tendons, the flexor digitorium profundus tendons, and the palaris longus tendon of the wrist in the region of the transverse carpal ligament of the wrist in the region of the transverse carpal ligament;
wherein a second pressure transmitting member is disposed on the flexible main body and adapted to apply focused pressure to the flexor carpi ulnaris tendon of the wrist in the region of the transverse carpal ligament;
wherein a third transmitting member is disposed on the flexible main body and adapted to apply focused pressure to the flexor carpi radialis tendon of the wrist in the region of the transverse carpal ligament;
wherein a forth pressure transmitting member is disposed on the flexible main body and adapted to apply focused pressure to the extensor dig itorum tendons and extensor indicis tendon of the wrist in the region of the extensor retinaculum; wherein the flexible, main body and pressure transmitting member allow near normal flexion and extension of the wrist, and
wherein none of the pressure transmitting members are positioned on a front portion or a back portion of the hand during use.

2. The wrist brace of claim 1, wherein the flexible, main body is made from an elastic material.

3. The wrist brace of claim 2, further including a fastener associated with the flexible main body for fixing the amount pressure that the flexible, main body exerts on the wearer's hand.

4. The wrist brace of claim 1, wherein the flexible, main body is designed to be worn on either the left hand or the right hand.

5. The wrist brace of claim 1, wherein the flexible, main body is a glove.

6. The wrist brace of claim 1, wherein the flexible, main body is an elastic strap having a opening for receiving the thumb of the user.

7. The wrist brace of claim 1, wherein the pressure transmitting member applies focused pressure without substantially impinging on areas adjacent to the tendons to which the pressure transmitting member is applying focused pressure.

8. A wrist brace, comprising:
a flexible elongate body having a opening for receiving the thumb of the wearer, the flexible body being adapted to be wrapped around a hand and wrist of the wearer, the body having an outer surface and an inner surface with the inner surface coming in contact with the hand of the wearer during use; and when in use, a plurality of unconnected and distinct pressure transmitting members apply focused pressure to the tendons of the wrist,
wherein a first pressure transmitting member is disposed on the main body and adapted to apply focused pressure to the flexor digitorum superficialis tendons and flexor digitorium profundus tendons of the wrist in the region of the transverse carpal ligament;
wherein a second pressure transmitting member is disposed on the flexible main body and adapted to apply focused pressure to the flexor carpi ulnaris tendon of the wrist in the region of the transverse carpal ligament;
wherein a third transmitting member is disposed on the flexible main body and adapted to apply focused pressure to the flexor carpi radialis tendon of the wrist in the region of the transverse carpal ligament;
wherein a fourth pressure transmitting member is disposed on the flexible main body and adapted to apply focused pressure to the extensor dig itorum tendons and extensor indicis tendon of the wrist in the region of the extensor retinaculum; wherein the flexible, main body and pressure transmitting member allow near normal flexion and extension of the wrist, and
wherein none of the pressure transmitting members are positioned on a front portion or a back portion of the hand during use.

9. The wrist brace of claim 8, further including a hook and loop fastener system associated with the flexible body.

10. The wrist brace of claim 8, wherein the pressure transmitting member applies focused pressure without substantially impinging on areas adjacent to the tendons to which the pressure transmitting member is applying focused pressure.

11. A method for preventing or reducing wrist pain on a user, comprising:
providing a flexible, main body having first, second, third and fourth unconnected and distinct pressure transmitting members disposed thereon; and positioning the first pressure transmitting member over the flexor digitorum superficialis tendons and flexor digitorium profundus tendons of the wrist in the region of the transverse carpal ligament to apply a focused pressure thereto;
positioning the second pressure transmitting member over the flexor carpi ulnaris tendon of the wrist in the region of the transverse carpal ligament to apply a focused pressure thereto;
positioning the third transmitting member over the flexor carpi radialis tendon of the wrist in the region of the transverse carpal ligament to apply a focused pressure thereto;
positioning the fourth pressure transmitting member over the extensor digitorum tendons and extensor indicis tendon of the wrist in the region of the extensor retinaculum to apply a focused pressure thereto, wherein the flexible, main body and pressure transmitting member allow near normal flexion and extension of the wrist; and
wherein none of the pressure transmitting members are positioned on a front portion or a back portion of the hand during use.

12. The method of claim 11, wherein the pressure transmitting member applies focused pressure without substantially impinging on areas adjacent to the tendons to which the pressure transmitting member is applying focused pressure.

* * * * *